United States Patent [19]

Nugent

[11] Patent Number: 4,827,944
[45] Date of Patent: May 9, 1989

[54] BODY FLUID SAMPLE COLLECTION TUBE COMPOSITE

[75] Inventor: Edward L. Nugent, North Caldwell, N.J.

[73] Assignee: Becton, Dickinson and Company, Franklin Lakes, N.J.

[21] Appl. No.: 76,446

[22] Filed: Jul. 22, 1987

[51] Int. Cl.$^4$ ............................................. A61B 5/00
[52] U.S. Cl. .................................. 128/771; 128/764; 604/318; 604/404
[58] Field of Search ............................... 128/760–764, 128/770, 771; 604/51, 52, 187, 236, 238, 403, 404, 318, 411–416; 428/35; 215/256, 246

[56] References Cited

U.S. PATENT DOCUMENTS

| | | | |
|---|---|---|---|
| 3,373,735 | 3/1968 | Gallagher | 128/771 |
| 3,465,907 | 9/1969 | Dorn et al. | 215/256 |
| 3,955,020 | 5/1976 | Cavanagh et al. | 428/35 |
| 4,134,512 | 1/1979 | Nugent | 128/764 |
| 4,463,861 | 8/1984 | Tsubone et al. | 428/35 |
| 4,658,833 | 4/1987 | Stuart | 128/771 |
| 4,724,973 | 2/1988 | Shah | 215/246 |

FOREIGN PATENT DOCUMENTS 0225337 7/1985 Fed. Rep. of Germany ...... 604/318

OTHER PUBLICATIONS

"Urine Collection Bag with Indicator Device", German Pat. No. 225,337A1, Gropp et al. (Medz) 1985.

Primary Examiner—Max Hindenburg
Attorney, Agent, or Firm—Robert P. Grindle

[57] ABSTRACT

A composite body fluid sample container is provided which incorporates at least one dry chemistry test strip into the structure with a shrink-wrap film whereby a plurality of chemically impregnated patches are exposed simultaneously in a self-contained device to provide instant response to a specimen introduced into the container. Moreover, the device separates the test strip from the remainder of the specimen so as to provide for additional testing if required. In addition, the device maintains the specimen, and the impregnated test strip isolated from exposure to contamination while at the same time keeping the specimen, if diseased, from contaminating handlers of the device. Finally, the device protects against breakage and any resulting leakage or contamination.

6 Claims, 3 Drawing Sheets

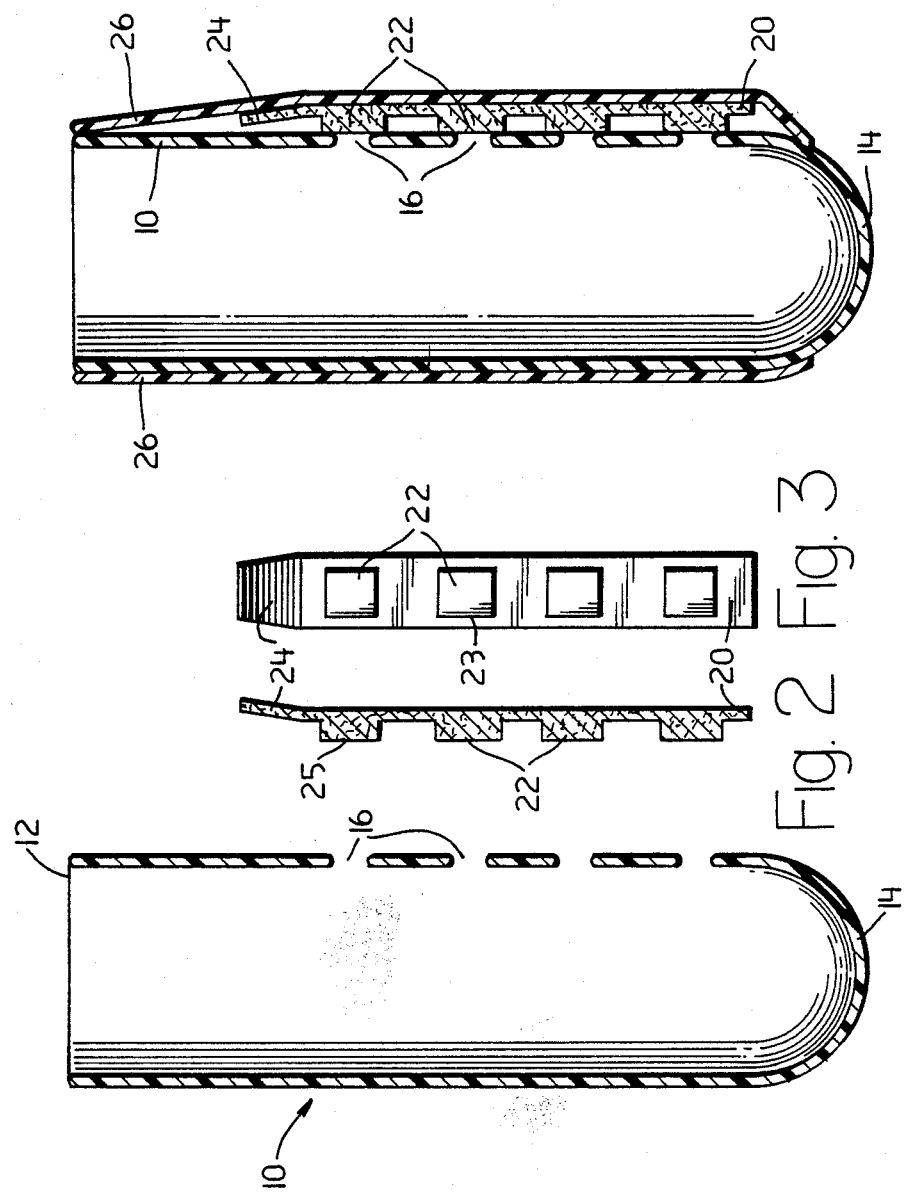

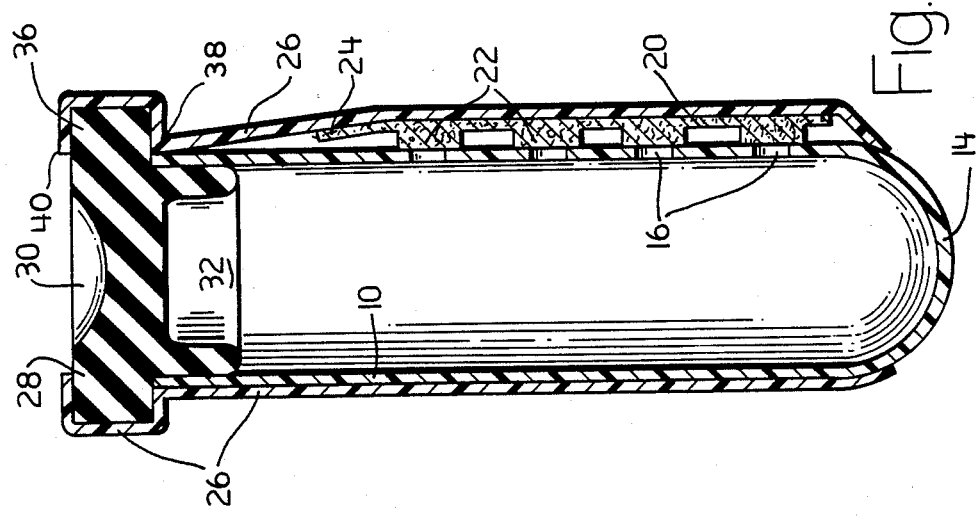
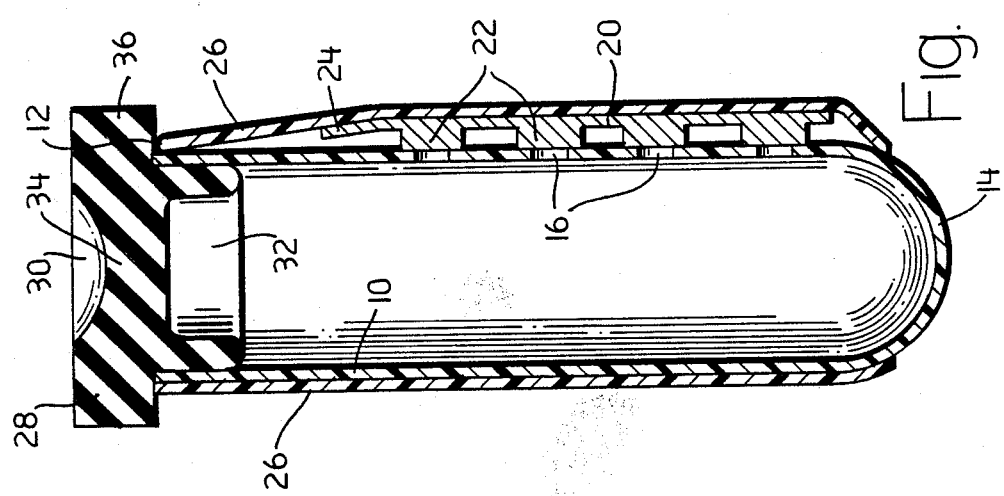

BODY FLUID SAMPLE COLLECTION TUBE COMPOSITE

BACKGROUND AND STATEMENT OF THE INVENTION

This invention is related to the subject matter described and claimed in co-pending application Ser. No. 049,240 filed May 13, 1987, which is hereby incorporated by reference in its entirety. This invention relates to containers for receiving body fluid samples, and for containing those samples for subsequent examination to determine the presence or absence of disease in the samples. More particularly, this invention relates to such containers having incorporated therewith a standard dry chemistry test strip for testing for the presence and/or absence of a plurality of potential diseases, or other body conditions, in the sample introduced into the container.

Generally speaking, such containers are in tube form, and they may or may not be evacuated, depending upon the particular sample being taken. As will be understood by practitioners-in-the-art, evacuated tubes are used in great numbers for taking blood and urine samples, with the tubes containing reagents for reacting with the samples for determining in subsequent clinical tests the presence or absence of disease. The tubes may also be non-evacuated tubes for taking samples for one reason or another. Urine samples may be taken in both evacuated and non-evacuated tubes. While non-evacuated tubes are utilized in great numbers, it is preferred to use evacuated tubes for many specific applications for maintaining a seal of the tube prior to use and for facilitating the entry of the sample into the evacuated tube for subsequent testing of the sample.

In taking urine samples in the past, it has been conventional for the sample to be introduced into a cup or other open container. Subsequently, a dry chemistry test strip is introduced into the urine sample for examination to determine the presence or absence of diseases, or other conditions of the sample taken. These tests include, for example, pH, protein, glucose, ketone, bilirubin, blood, urobilinogen. However, in using such open containers, there is a risk that the sample will be contaminated prior to the testing taking place. Moreover, there is the danger that the person handling the sample will be contaminated in one way or another by exposure to the sample.

With this invention, by contrast, a test strip is incorporated into and made a part of the container assembly receiving a blood and/or urine sample for testing. That is, a conventional transparent tube, preferably plastic, has a plurality of bores through one portion of the wall thereof. Placed immediately adjacent each bore is a different dry chemistry test patch for individual tests. The patches are positioned to be immediately adjacent the bores in the tube so that when a sample is introduced into the tube, a portion of the sample passes through each of the bores and is absorbed into each of the adjacent individual test patches.

In this way, a plurality of tests for the presence or absence of conditions in the sample take place almost simultaneously with the introduction of the sample into the assembly. Moreover, the sample is maintained in an uncontaminated state in the tube proper so that a portion of the sample remains for further testing, if required.

The arrangement of invention here includes the utilization of a transparent shrink-wrap over the tube and the test strip so as to maintain the container in a sealed uncontaminated condition prior to use. Moreover, with the shrink-wrap in combination with the tube body and the test strip together with a conventional stopper on the tube, the container of the invention may be evacuated so as to facilitate later introduction of the sample into the tube. The tube is maintained in a sealed uncontaminated state until use so that the sample remains uncontaminated until all of the testing is completed.

The assembly of the invention herein utilizes a preshrunk film disposed over the outer surface of a tube or other container for taking a body fluid sample. That is, a film is pre-shrunk over the previously developed container. In this connection, the container may be glass or thermoplastic. A thermoplastic material is preferred because it is much simpler, and far less costly, to incorporate the bores utilized with the invention herein in a plastic tube as opposed to a glass tube.

At any rate, a test strip which may be a conventional dry chemistry strip such as "CHEMSTRIP 7L" ™ by Boehringer Mannheim Diagnostics or "MULTISTIX" ™ by Ames Division of Miles Laboratories may be incorporated into the structure in accordance with this invention. That is, the test strip may be placed so that the individual test patches having incorporated therein certain chemicals for reacting and indicating by color the presence or absence of disease or other condition in a urine sample are placed adjacent the bores in the tube container of the invention. Subsequently, the entire structure including the test strip is incorporated into the clear shrink-wrapped film as discussed above. By having the entire outer surface, or a substantial portion thereof, covered by a wrapped plastic film the plastic wrap around the tube contains the sample therein. Moreover, the plastic wrap shields the technician from any contamination from a sample by leakage or cracking of the container in some manner. Nevertheless, the response of each test patch is immediately visible once a sample is introduced into the container.

It will be understood that the tube may be evacuated or not evacuated in accordance with this invention. The presence of the film firmly adhering to the outer surface of a container and test strip holding a body fluid sample has the effect of maintaining the general integrity of the container so that it may be properly utilized and disposed of without any contamination to the user. Moreover, the wrap makes the container stronger overall because of the cushioning characteristics of the wrap.

As purely illustrative of a plastic film material which may be used as a shrink-wrap over a fluid specimen container in accordance with this invention, one may note that polyvinyl chloride, polyester copolymers or polystyrene films may be utilized for shrink-wrapping such containers. One particularly appropriate material is polyvinyl chloride film such as "SkinTight" ®, a heat-shrinkable polyvinyl chloride film supplied by Gilbreth International Corporation, Bensalem, Pa. 18020. Such polyvinyl chloride films obtain the desired shrinking property by first being extruded, followed by then holding and restraining one dimension of the film while cooling the material, and not restraining the other dimension thereof. This has the effect of pre-stressing the material in the direction which it is held. Subsequently, with the application of heat, the material will then shrink about five to ten percent in the direction not held or restrained while shrinking about fifty-five to seventy-five percent in the pre-stressed direction so that it "shrinks-down" onto the vessel being covered.

It may be appropriate to apply a heat-activated adhesive to the inner surface of the film which will adhere to the vessel being encompassed by the shrink-down film. The heat-activated adhesive may be printed or applied to the inner surface of the film and when the film is heated for shrink-down onto the container, the adhesive becomes activated and helps adhere the film to the object being wrapped. Any conventional heat-activated adhesive may be used for such application.

As a further feature of the invention, the shrunk-down film may be applied to an evacuated container, for example, once the stopper therefor has been put into place and the vacuum applied, holding the stopper in a sealed position. Subsequent application of the plastic wrap which is to be shrunk-down may be over both the container itself and it may extend up and over the stopper. By doing so, a further sealing of the stopper tube interface takes place.

A registered serration may be incorporated into the shrink film at the stopper/glass interface in order to develop a tamper-proof closure. This may be appropriate for drug abuse testing, as well as specimen identification and quality control.

Printing may be placed on either side of the shrinkable tube of film material which is to be shrunk-down onto the container of interest. For example, a product identification, brand name, or company logo may all be included on the inner or outer surface of the film prior to introduction onto the container. Also, a matte finish or a corona discharge surface may be developed on the outer surface of the film to be shrunk onto the container so as to make the surface appropriate for receiving subsequently added written identification information for a sample contained in the container. Furthermore, pressure sensitive adhesive labels may be placed on the outer surface of the shrunk-down film so as to accommodate various hospital over-labels, for example.

With the foregoing and additional objects in view, this invention will now be described in more detail, and other objects and advantages thereof will be apparent from the following description, the accompanying drawings, and the appended claims.

As purely illustrative of an arrangement of wrapped container which may be used for carrying out this invention, one may note the attached drawings in which several embodiments of such a container are shown utilizing the wrapped container/dry chemistry strip combination feature of the invention.

IN THE DRAWINGS

FIG. 1 is a longitudinal sectional view of a tube-shaped body fluid sample container illustrating the invention, and showing the bores incorporated into one portion of the wall of the container;

FIG. 2 is a side elevational view of a representative dry chemistry strip;

FIG. 3 is a plan view of the strip of FIG. 2;

FIG. 4 is a longitudinal sectional view of an evacuated tube with the test strip, as shown in FIGS. 2 and 3 incorporated with the tube in a shrunk-down film assembly illustrating one embodiment of the invention;

FIG. 5 is a longitudinal sectional view of the assembly of FIG. 4 with the stopper placed in the open end thereof;

FIG. 6 is a longitudinal sectional view of a further embodiment of the invention illustrating an evacuated tube-test strip assembly with the stopper in place, and with the shrunk-down film encompassing both the tube container and the stopper therefor;

Figure 8:
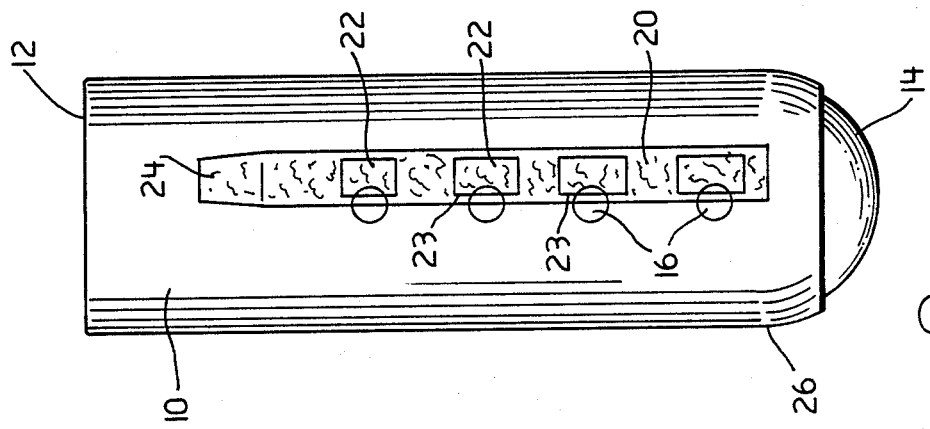
Figure 7:
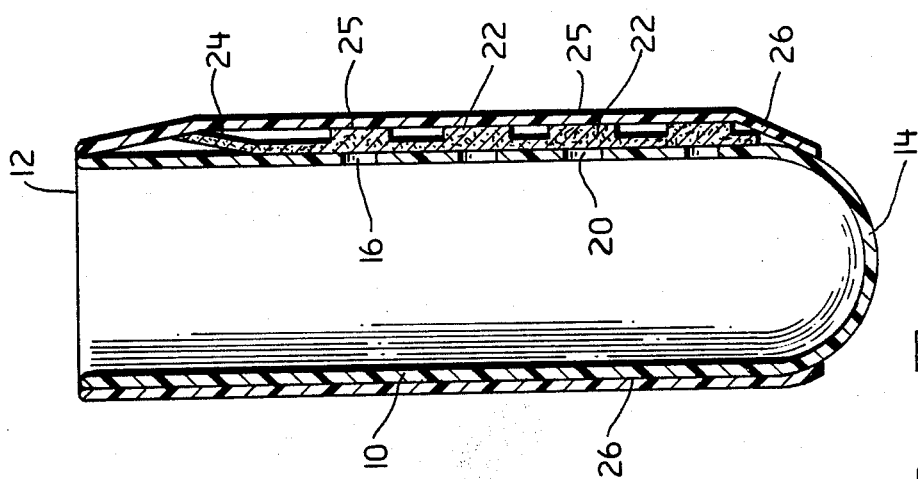

FIG. 7 is a longitudinal sectional view of a further embodiment of the invention illustrating a tube-test strip assembly similar to the embodiment shown in FIG. 4, but with a different type of test strip positioned with the test patches facing outwardly from the adjacent bores in the tube; and FIG. 8 is a view in elevation of the tube of FIG. 7, showing the positioning of the test strip and related test patches with the bores in the tube.

DETAILED DESCRIPTION OF THE INVENTION

Referring to the drawings in which like reference characters refer to like parts throughout the several views thereof, FIG. 1 shows a tube generally designated 10 which may be plastic or glass, and preferably a thermoplastic, having an open end 12 and a closed end 14. As shown in FIG. 1, tube 10 has a plurality of bores 16 placed along the vertical extent thereof, with these bores being for the passage of a sample introduced into tube 10 through the bores to impregnate adjacent dry chemistry patches, to be discussed in more detail below.

FIG. 2 shows a conventional dry chemistry test strip 20 having a plurality of test strip patches 22 thereon. Usually, the strip 20 will have a tab 24 on one end thereof for handling during use, although the tab 24 is not necessary for the invention here. As mentioned above, the patches 22 may have incorporated thereon a plurality of different chemical reagents for reacting with a urine sample, for example, to indicate certain conditions such as pH, the presence of blood in the urine, glucose, as well as other desired testing reagents. It will be understood by practitioners-in-the-art that the number of patches 22 may be increased or decreased from the four shown in FIGS. 2 and 3 to accommodate the number of bores 16 in tube 10 and the number of desired tests to be accommodated within a single sample device in accordance with this invention. Some forms of test strips absorb sample liquids only through the side edges 23 of patches 22 and show color response to samples only at the outer surface 25, thus necessitating different positioning of strips 20 adjacent bores 16, as will be discussed below.

Referring now to FIG. 4, tube 10 is shown with the test strip 20 in place so that the individual patches 22 are placed over the individual bores 16 therefor. A plastic film wrap 26 is pre-shrunk over the tube, strip assembly and incorporates the assembly in a sealed arrangement therefor. While wrap 26 leaves closed end 14 exposed, it will be understood that wrap 26 may incorporate the entire tube 10, as shown in the above-noted co-pending application. Thus, when a sample is introduced into tube 10, it will pass through bores 16 and impregnate simultaneously and immediately, the plurality of reagent patches 22 on test strip 20 so that an indication can be made immediately of a suspected condition or conditions for which the testing is taking place.

Referring now to FIG. 5, the arrangement of FIG. 4 is shown with stopper 28 therefor in place. Stopper 28 is comprised of an elastomer, usually of a natural or synthetic material or a combination of the two. It is placed in tube 10 simultaneously with the evacuation thereof, if the tube 10 is to be an evacuated tube. Stopper 28 includes an annular upper portion 36 which extends out over the top edge of the open end 12 of tube 10. Stopper 28 includes an upper well 30 and a lower well 32 which combine to provide a relatively thin diaphragm area 34 for the introduction of a needle therethrough to introduce a sample into evacuated tube 10.

Referring now to FIG. 6, an additional embodiment is shown similar to that of FIG. 5 and with the same parts being identified with the same identifying numbers. As shown in FIG. 6, however, the shrink-wrap film 26 extends up and over stopper 28 to a point 40 on the top surface of stopper 28. Thus, the shrink-wrap film serves to provide an additional seal between the stopper 28 and the tube 10 for maintaining a vacuum therein and for also maintaining a non-contaminating seal of the container 10 if it is in a non-evacuated form.

With this embodiment, a serration 38 may be incorporated adjacent the separation line of stopper 28 with container 10 so as to provide an indication of tampering with the container prior to use. This is particularly important for drug abuse applications. A broken serration line may indicate that someone attempted to introduce a non-related urine sample, for example, into the tube prior to the testing thereof.

Referring now to the embodiment shown in FIGS. 7 and 8. In this embodiment, patches 22 are formed to absorb liquid from a sample only through the side edges 23 thereof (FIG. 3). Thus, in this embodiment, the strip 20 is positioned so that the patches 22 face away from the adjacent tube 10 wall as shown in FIG. 7. Also, the color response shows only at surfaces 25 (FIG. 2) of patches 22, so that this surface 25 is faced outwardly as shown in FIG. 7. Also, as shown in FIG. 8, strip 20 is positioned partially to one side of bores 16 so that the side edges 23 of patches 22 receive and absorb liquid sample therethrough.

Thus, as will be apparent from the foregoing, there are provided in accordance with this invention, containers for receiving and holding body fluid samples which may or may not contain a disease. The arrangement herein of pre-shrunk film covering the entire container assembly is particularly appropriate for evacuated containers since it maintains the container in non-contaminated state while at the same time providing relative ease of introduction of a sample into the container. More importantly, the container of the invention includes provision for immediate and simultaneous indication of the presence or absence of a number of conditions in a sample so as to indicate the need for further sampling. The container segregates the dry chemistry test strip which provides the immediate indication of the presence or absence of conditions so that the remainder of the sample may be used for further testing. It will be understood, however, that the invention provides a very useful and inexpensive approach to containing samples in evacuated or non-evacuated containers without contamination and with a simultaneous testing feature.

Because of the tremendous concern with the use of drugs, moreover, the arrangement herein provides for a tamper-proof test arrangement so that it will be clear when a sample has been contaminated prior to the testing thereof.

While the particular arrangements of body fluid sample containers disclosed herein form preferred embodiments of this invention, this invention is not limited to those particular embodiments and changes can be made therein without departing from the scope of the invention which is defined in the appended claims. For example, while the particular embodiments shown are all tube-shaped, it will be understood that the shrinkable films of the invention herein may be arranged to conform to any configuration of container and the stopper or cap therefor. Moreover, while all of the bores in the container are shown in a single line with a single test strip, it will be understood that several test strips with several lines of bores may be incorporated into a tube for a larger series of simultaneous tests of the sample.

Thus, any form of container for holding fluids wherein thermoplastic as the preferred material may be used. Moreover, even though the film is particularly directed to maintaining the sealing integrity of a plastic container, it will be understood that the invention may be utilized for increasing the integrity of thin-walled glass containers as well.

What is claimed is:

1. A composite sample container assembly for receiving and containing body fluid samples for testing in which a plurality of tests are carried out simultaneously upon introduction of a fluid sample into the container, but which sample remains segregated in the container for subsequent further testing, characterized by
   (a) an evacuated substantially rigid tube-shaped thermoplastic container defining a sample containing chamber;
   (b) said container having a closed end and an open end;
   (c) an elastomeric stopper for said open end to maintain a vacuum in said sample containing chamber;
   (d) a plurality of spaced apart bores in the wall of said container, and positioned between said open end and said closed end;
   (e) a plurality of dry chemistry impregnated patches, with each patch positioned adjacent one of said bores and in communication with but outside said chamber;
   (f) each said patch containing a different reagent for reacting with a body fluid sample introduced into said chamber and passing through said bores;
   (g) a transparent thermoplastic film shrunk down upon said patches and at least a major portion of the outer surface of said container by the application of heat; and
   (h) said transparent thermoplastic film allowing observation of the response of the reagents in each said patch upon a sample being drawn into said chamber by a vacuum applied thereto; while the sample remains in said chamber for further examination.

2. The assembly of claim 1, further characterized by
   (a) said film includes registered tamper serrations adjacent said stopper/container interface.

3. The assembly of claim 1, further characterized by
   (a) the surface of said film facing said outer surface of said container being coated with a heat-activated adhesive.

4. The assembly of claim 1, further characterized by
   (a) said shrunk-down thermoplastic film is a member selected from the group consisting of polyvinyl chloride, a polyester, and polystyrene.

5. The assembly of claim 4, further characterized by
   (a) said film is comprised of prestressed polyvinyl chloride film.

6. The assembly of claim 1, further characterized by
   (a) said transparent thermoplastic film is shrunk down over a portion of said elastomeric stopper.

* * * * *